(12) United States Patent
Rini et al.

(10) Patent No.: US 11,511,053 B2
(45) Date of Patent: Nov. 29, 2022

(54) PEN NEEDLE HUB INJECTION DEPTH OPTIMIZATION

(71) Applicant: Embecta Corp., Andover, MA (US)

(72) Inventors: Christopher Rini, Raleigh, NC (US);
Richard Klug, Roxboro, NC (US);
Bruce Roberts, Hillsborough, NC (US);
Didier Morel, Franklin Lakes, NJ (US);
Ronald Pettis, Cary, NC (US)

(73) Assignee: Embecta Corp., Andover, MA (US)

( * ) Notice: Subject to any disclaimer, the term of this patent is extended or adjusted under 35 U.S.C. 154(b) by 504 days.

(21) Appl. No.: 16/485,536

(22) PCT Filed: Feb. 16, 2018

(86) PCT No.: PCT/US2018/018490
§ 371 (c)(1),
(2) Date: Aug. 13, 2019

(87) PCT Pub. No.: WO2018/156430
PCT Pub. Date: Aug. 30, 2018

(65) Prior Publication Data
US 2020/0384210 A1    Dec. 10, 2020

Related U.S. Application Data

(60) Provisional application No. 62/459,727, filed on Feb. 16, 2017.

(51) Int. Cl.
*A61M 5/32* (2006.01)
*A61M 5/315* (2006.01)
(Continued)

(52) U.S. Cl.
CPC ...... *A61M 5/3293* (2013.01); *A61M 5/31535* (2013.01); *A61M 5/343* (2013.01); *A61M 5/46* (2013.01)

(58) Field of Classification Search
CPC .. A61M 5/3293; A61M 5/31535; A61M 5/46; A61M 5/32; A61M 5/343
See application file for complete search history.

(56) References Cited

U.S. PATENT DOCUMENTS

| 3,797,490 A | 3/1974 | Hurschman et al. |
| 2007/0118077 A1 | 5/2007 | Clarke et al. |

(Continued)

FOREIGN PATENT DOCUMENTS

| CN | 1756573 B | 6/2011 |
| CN | 202044604 U | 11/2011 |

(Continued)

OTHER PUBLICATIONS

International Search Report dated May 29, 2018, which issued in the corresponding PCT Patent Application No. PCT/US2018/018490.

(Continued)

*Primary Examiner* — Nathan R Price
*Assistant Examiner* — Anh Bui
(74) *Attorney, Agent, or Firm* — Greenberg Traurig, LLP; David J. Dykeman; Roman Fayerberg

(57) ABSTRACT

A needle hub (10) for a pen needle is provided with an enlarged surface for contact with the skin of a patient. The enlarged surface is provided with a surface having a dimension and shape to enable a needle or cannula to penetrate the skin to a desired depth and permit substantially the entire exposed length of the needle or cannula to penetrate the skin to the desired depth. The surface of the needle hub can be formed by an inner cone shaped member (26) forming a first contact surface with a surface area of about 1-5 mm² and an outer ring (28) at a peripheral edge forming a second contact surface with a combined surface area of about 15 to 50 mm².

21 Claims, 4 Drawing Sheets

(51) Int. Cl.
    *A61M 5/46*     (2006.01)
    *A61M 5/34*     (2006.01)

(56) References Cited

U.S. PATENT DOCUMENTS

| | | | |
|---|---|---|---|
| 2008/0045900 A1 | 2/2008 | Alchas et al. | |
| 2009/0069755 A1 | 3/2009 | Horvath | |
| 2011/0275994 A1 | 11/2011 | Wase et al. | |
| 2013/0096502 A1 | 4/2013 | Kawamoto et al. | |
| 2014/0188046 A1 | 7/2014 | Dibiasi et al. | |
| 2015/0051582 A1 | 2/2015 | Pettis et al. | |
| 2018/0021526 A1* | 1/2018 | Sullivan | A61M 5/3202 604/506 |

FOREIGN PATENT DOCUMENTS

| | | | |
|---|---|---|---|
| CN | 102821807 | A | 12/2012 |
| CN | 102413858 | B | 3/2017 |
| CN | 210044614 | U | 2/2020 |
| CN | 106232164 | B | 8/2021 |
| JP | 2018503467 | A | 2/2018 |
| WO | 2016123494 | A1 | 8/2016 |
| WO | 2018018490 | A1 | 2/2018 |

OTHER PUBLICATIONS

Barbe, L., et al., Needle Insertion Modelling; Identifiability and Limitations, Biomedical Signal Processing and Control 2 (2007) pp. 191-198.

Lo Presti, et al., "Skin and subcutaneous thickness at injecting sites in children with diabetes: ultrasound findings and recommendations for giving injection", Pediatric Diabetes, vol. 13, Issue 7, pp. 525-533, Nov. 2012.

* cited by examiner and bruising associated with the injection. The primary design features, needle length/gauge and hub face geometry, in conjunction with mechanics of the delivery system and injection technique, dictate injection success.

PEN NEEDLE HUB INJECTION DEPTH OPTIMIZATION

This application claims priority to U.S. Provisional Application No. 62/459,727, filed Feb. 16, 2017, which is incorporated by reference in its entirety.

FIELD OF THE INVENTION

The present invention is directed to a needle hub and needle hub face configured for controlling the insertion depth of a needle or cannula. The invention is also directed to a pen needle having a needle hub with interfacing features to limit the depth of penetration of the needle during the initial insertion and during the injection of a substance to the patient. The contact face is configured to optimize the depth of penetration or insertion where substantially the entire length of the needle or cannula exposed from the hub can be inserted into the skin, which provides improved consistency of depth of penetration. The needle hub has a hub face with certain areas for concentrating the surface pressure applied to the surface of the skin in selected areas to control the depth of penetration into the skin.

DESCRIPTION OF THE RELATED ART

The insertion of a needle into the skin of a patient is determined primarily on the features of the needle and not the features or structure of the needle support as disclosed in Needle Insertion Modeling; Identifiability and Limitations, L. Bathe, Biomedical Signal Processing and Control 2 (207) 191-198. Needle insertion into the skin of patient is generally classified into three phases that influence the injection depth. The first phase corresponds to the initial contact of the needle with the skin where the tissue deforms without puncturing the surface of the skin. A second phase refers to the puncture of the skin and the relaxation of the skin when the insertion force of the needle is stopped. The third phase is where the needle is extracted and pulls or stretches the skin outward as the needle is extracted.

Various injection devices have been produced where the supporting structure does not contact the skin during injection or extraction of the needle. Other devices have been proposed where the end face of the device is positioned to contact the surface of the skin to limit the depth of penetration into the patient.

Pen-injector delivery devices have been developed to facilitate self-administration of parenteral medications. Pen needles are a component of needle-based injection systems and consist of a doubled ended cannula assembled into a plastic hub using adhesive. The hub has internal threads, which allow it to be attached to the pen-injector device. Pen needle attachment allows the proximal end of cannula to penetrate through the rubber septum of the medicament cartridge to create the fluid flow path. For many diabetics maintaining blood glucose control is achieved by performing multiple daily injections of insulin into the subcutaneous (SC) tissue using pen injector delivery devices developed to be a convenient, discreet alternative to the vial and syringe. Numerous pen injectors are commercially available in either disposable or multi-use configurations, each offering various patient-centric features. The distal pen needle cannula interfaces with the delivery site providing a conduit for delivery. Pen needle designs are intended to enable consistent delivery to the target tissue space, minimize leakage of injectate, and reduce pain/discomfort and site effects such as bleeding and bruising associated with the injection. The primary design features, needle length/gauge and hub face geometry, in conjunction with mechanics of the delivery system and injection technique, dictate injection success.

Injections may be performed in the intradermal region, the subcutaneous region and the intramuscular (IM) region of the skin. For many types of injectable medications, including insulin, the SC region is preferred for administering an injection. See, for example, Lo Presti, et al., Skin and subcutaneous thickness at injecting sites in children with diabetes: ultrasound findings and recommendations for giving injection, *Pediatric Diabetes* (2012).

Needle lengths, such as needles having a length of about 4 mm to 5 mm are adapted to inject a medication to a specified target depth in a subcutaneous region. The present invention provides a structure so that a needle can be consistently inserted to a desired target depth. Prior pen needles have the cannula supported on an axial post extending from the hub. The post forms a narrow portion and a relatively wider base that does not contact the skin during the injection. In other pen needles known in the art, a distal face of the hub placed against the injection site may be relatively large, and may be provided with a slight taper at the edge. The edge of the hub can engage the skin when the cannula is inserted at an angle relative to the surface of the skin of the patient.

While the prior devices are generally suitable for the intended use, there is a continuing need for improved devices for controlling the depth of penetration of a cannula for delivering a drug or medicament to a selected target area.

SUMMARY OF THE INVENTION

The present invention is directed to an injection device and particularly to a needle hub for use with an injection device such as a pen-injector. The invention is further directed to an injection device for injecting a drug, medicament, or other substance to a patient at a desired depth relative to the surface of the skin. The needle hub has a hub face forming a contact surface with the skin and includes a predetermined shape, dimension, and geometry for controlling and optimizing the depth of penetration by a needle or cannula inhibiting penetration by the needle or cannula below a desired depth. The needle hub optimizes the depth of insertion such that the entire length of the exposed cannula or needle is inserted into the tissue, which provides improved consistency of depth of injection. The needle hub has a skin contact face with a shape and configuration to provide consistency of the depth of cannula insertion over a range of insertion forces applied by a user.

The needle hub face in one embodiment of the invention has a skin contact surface with a surface geometry determined by a shape and dimension that controls the depth of penetration of the needle. The face of the needle hub provides a surface area that concentrates the pressure applied to the skin at the injection site to maximize insertion depth while controlling the depth of penetration. In one embodiment, the needle hub has a shape and dimension complementing the needle length to minimize intramuscular penetration by the needle or cannula. The needle hub face can have dimension and configuration to distribute the force across a selected surface area of the skin to inhibit penetration below a predetermined depth while enabling substantially the entire length of the needle or cannula to penetrate the skin or tissue to the desired depth.

In one embodiment of the invention, an injection device is provided having a needle hub with a contact face having an area around the base of the needle to concentrate the pressure or force against the skin and perimeter features to control the insertion depth during insertion by limiting deformation of the skin during insertion. The contour of the contact face provides a maximum penetration depth of the needle for a given length of the needle. A perimeter of the hub has a shape to distribute the pressure or force applied by the user to a predetermined surface area of the skin upon full engagement of the needle hub with the skin surface. The perimeter of the needle hub has a shape and dimension to limit needle penetration and skin displacement by distributing the insertion force across a surface area of the skin to control the deflection and distortion of the skin at the injection site.

Another feature of the invention is to provide a needle hub with a contact surface having a predetermined contour to provide a desired pressure distribution with improved comfort perception by the patient. The contact surface of the needle hub has a conical or convex shape in the embodiment shown.

In one embodiment of the invention, the needle hub has a contact surface with a shape and dimension to provide a consistent delivery of a substance over a range of delivery volumes and provide consistent and reproducible intra- and inter-operator delivery results.

The needle hub of the invention also provides a skin contact face that minimizes injection side effects, such as leakage, edema and erythema at doses of 1-60 U. The contact surface has a shape and dimension to provide a low level of perceived pain and discomfort by the user. The needle hub of the invention also provides a lower/shorter perceived profile that reduces use anxiety.

One embodiment of the invention provides a needle hub primarily for pen-injector devices where the skin contact face of the needle hub has a shape and dimension to reduce the influence of injection techniques between different users and to provide consistent introduction of short pen needles for subcutaneous delivery. The needle hub is configured for providing optimum depth of penetration and delivery of the injected substance by controlling the deformation of the surface of the skin when the needle hub is pressed against the skin of the patient.

These and other objects of the invention are attained by providing a needle hub for a pen needle having a skin contact face with a shape to form an initial contact surface area of about 1 mm$^2$ to 5 mm$^2$. In another embodiment, the initial surface contact surface are can be about 1-10 mm$^2$. The needle hub has a shape where the contact face when in full contact with the skin has a surface area of about 5-50 mm$^2$. In one embodiment, the surface area in hill contact can be about 15 to about 35 mm$^2$.

The features of the invention are basically attained by providing a needle hub configured for coupling to a pen injector delivery device where the needle hub comprises a body with a proximal end and a distal end, where the proximal end is configured for coupling to the pen injector delivery device. A cannula is coupled to the body and extends from the distal end for insertion into the patient. The distal hub end interfaces the surface of the skin of a patient upon insertion of the cannula into the skin of the patient. The contact surface has a first portion surrounding the base of the cannula and forming an annular first contact surface having a surface area of about 1-5 mm$^2$. The contact surface has a second portion surrounding and spaced radially outward from the annular first contact surface forming an annular second contact surface, where the first contact surface and second contact surface have a combined surface area of about 15-50 mm$^2$. In another embodiment, the annular first contact surface and the annular second contact surface can have a combined surface area of about 15 mm$^2$ to about 35 mm$^2$. In one embodiment, an inner cone shaped member forms the first contact surface and extends axially a distance of about 0.5 mm from an outer ring forming the second contact surface.

The features of the invention are further attained by providing a method for injecting a medication with a medication pen by providing the medication pen with a needle hub having a body for coupling to the pen needle, a post extending from a distal end of the body, and a cannula coupled to the post. The post has a contact surface for contacting the skin of a patient upon insertion of the cannula into the skin. The contact surface has a first portion surrounding the cannula forming an annular first contact surface with a surface area of about 1-5 mm$^2$ and a second portion surrounding and spaced radially outward from the first portion and forming an annular second contact surface, where the first and second contact surfaced have a combined surface area of about 15-35 mm$^2$.

One feature of the invention is to provide a needle hub with a skin contact surface having a substantially conical shape forming a convex surface. In one embodiment the conical shaped skin contact surface has a centrally located cone-shaped annular portion projecting from a distal face of the needle hub having an axial height of about 0.3 to 0.7 mm relative to the convex surface. A cannula extends from a center portion of the annular portion for penetrating the skin. In one embodiment of the invention, the convex contact surface of the needle hub has an axial height of about 0.5 to 2.0 mm and width of about 5.0 to 8.0 mm and typically about 5.0 to 7.0 mm to provide sufficient surface area and a suitable shape to contact the skin and provide the controlled depth of penetration by the cannula into the skin.

Another feature of the invention is to provide an injection device having a cannula for penetrating the skin and where the device has a skin contact surface around the base of the cannula having a substantially convex surface with a width and height to control the depth of penetration. The convex surface has a height and a width to control the deformation of the skin during the insertion of the cannula to inhibit the cannula from penetrating the skin to the intramuscular layer.

A convex curved contact face of the needle hub provides a surface area for contacting an injection site on a patient to provide greater patient comfort and stability. Insulin and other diabetes related drugs are often delivered to the subcutaneous regions so that it is desirable to control the depth of penetration of the needle.

It will be understood that each of the preferred or optional features of the various embodiments may be combined with other features and features described in combination with one or more particular features may also be combined with one or more other features of the other embodiments.

These and other features of the invention will become apparent from the following detailed description of the invention, which in conjunction with the drawings disclose various embodiments of the invention.

BRIEF DESCRIPTION OF THE DRAWINGS

The following is a brief description of the drawings in which.

DETAILED DESCRIPTION OF EXEMPLARY EMBODIMENTS

Figure 1:
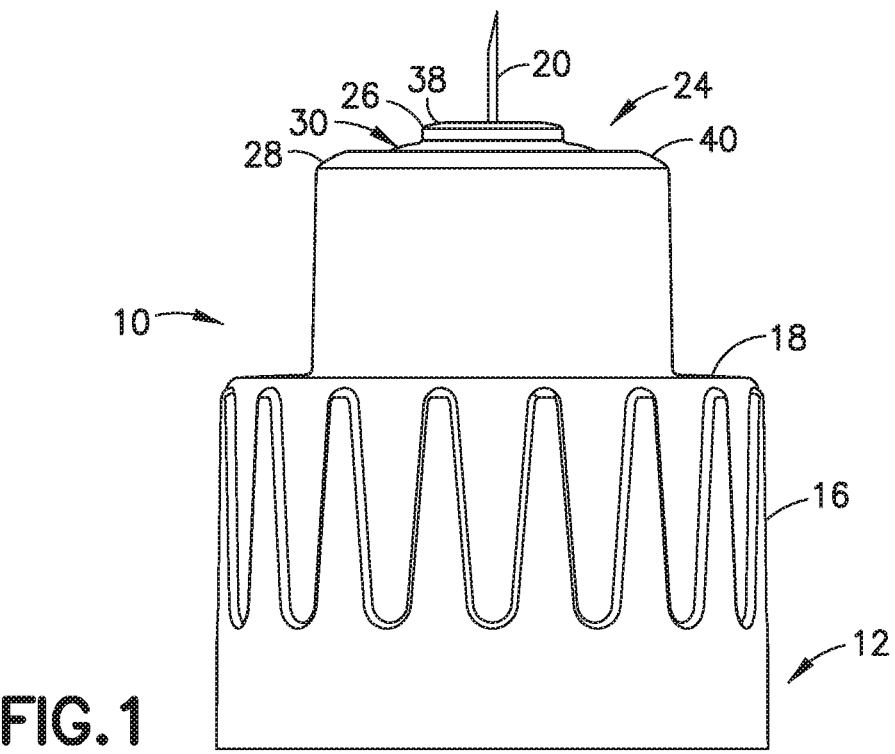
FIG. 1 is a side view is a side view of the needle hub in one embodiment of the invention.
Figure 2:
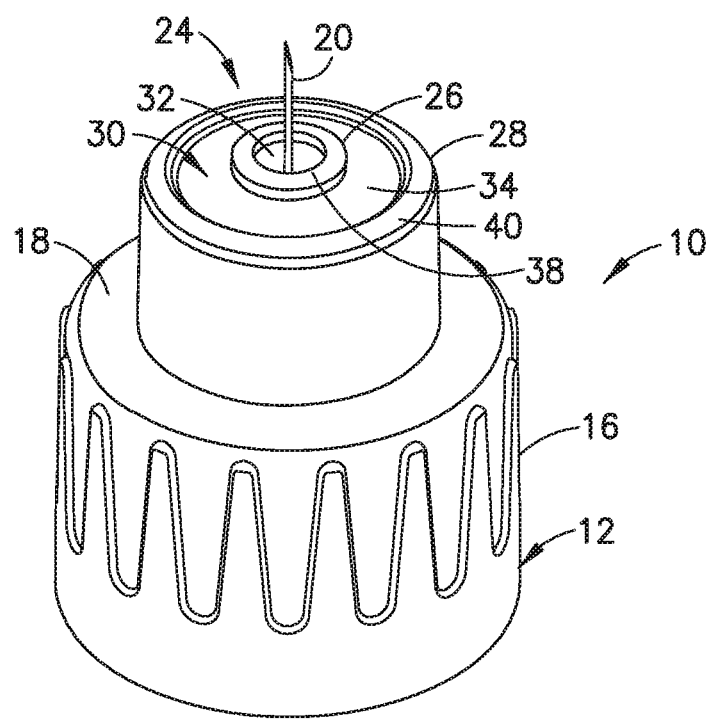
FIG. 2 is a top perspective view of the needle hub of FIG. 1.
Figure 3:
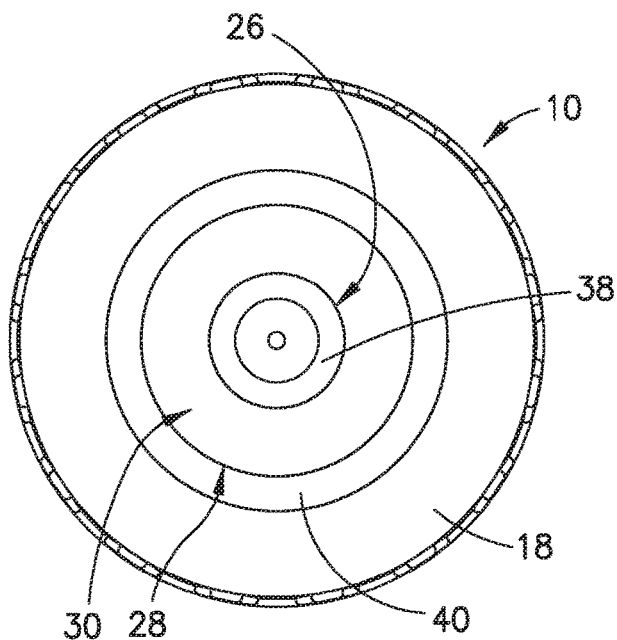
FIG. 3 is a top view of the needle hub in the embodiment of FIG. 1.

The pen needle of the invention refers to a needle hub attached to a pen-injector device for injecting a medication or other substance into a patient. The terms needle and cannula are used herein interchangeably to refer to a thin tubular member having a sharpened end for insertion into an injection site on a subject. A distal direction is in the direction toward the injection site, and the proximal direction is the opposite direction. The axial direction refers to a direction along or parallel to the longitudinal axis of the needle and the needle hub and the radial direction refers to a direction perpendicular to the axial direction. The pen-injector device can be a standard device as known in the art where the needle hub can be attached to the end of the pen-injector for delivering the substance to a patient. After use, the needle hub is removed and discarded and replaced with a new needle hub for a subsequent injection.

The intradermal layer in adults generally has a thickness of around 2 to 3 mm, so that intradermal injection depth is in a range of about 0 to 3 mm as measured from the outer surface of the skin. The thickness of the subcutaneous layer varies depending on the age of the patient, gender, body mass index (BMI), and the part of the body where the injection is administered. The subcutaneous region has an average thickness of about 7 mm to about 15 mm. Insulin is preferably delivered to the subcutaneous region.

The invention is directed to an injection device and particularly a needle hub having a cannula with a predetermined length for penetrating the skin to a predetermined penetrating depth. The needle or cannula can be for example, 3-8 mm and can be 31-33 gauge. In other embodiments, the needle or cannula can be other gauges as suitable for the intended purpose. In one embodiment, the needle can be 4-8 mm. In other embodiments, the can be 27-33 gauge. The needle hub has a skin contact surface for contacting and deforming the skin when the cannula penetrates the skin to provide controlled depth of penetration. The contact surface has a predetermined shape, width and height to control the skin deformation during insertion of the cannula to limit the depth of penetration into the skin by dispersing the insertion force over a suitable surface area of the skin. An application force with a device having a small narrow skin contact surface of about 3 mm or less can compress the skin around the cannula when the device is pressed against the skin during use. The focused compression can cause the cannula to penetrate into the skin to below a desired depth. The outer perimeter of the needle hub of the invention distributes the pressure to limit the compression of the skin and depth of penetration of the cannula. In one embodiment, the needle hub has a surface area that contacts the skin with a shape and configuration so that the entire length of the cannula is inserted into the tissue by a normal or customary insertion force applied by the user. The shape and configuration of the contact surface provides an improved consistency across a range of application forces of injection depth into the skin.

The skin contact surface of the pen needle device surrounding the cannula has a width and height configured for contacting the skin to distribute the contact pressure and limit or control the depth of penetration of the cannula. In one embodiment of the invention, the pen needle device is configured to obtain a cannula penetration of about 4 mm. The skin contact surface is further configured to control the shape, width, and depth of deformation of the skin surface when the device is pressed against the skin during the penetration of the cannula. The width corresponds to the surface area that contacts the skin during the initial insertion of the cannula into the skin and the surface contacting the skin during the injection or delivery of the drug at a typical force applied by the user. The height refers to the axial distance between the outer peripheral edge of the contact surface and the base of the cannula forming a proximal end of the contact surface. The surface area and shape of the contact surface can be configured to enable the entire or substantially the entire length of the needle or cannula to penetrate the skin while controlling the depth of penetration.

The needle hub in one embodiment has a first contact surface area for making first contact with the skin of about 1.0 mm$^2$ to about 5.0 mm$^2$ surrounding the cannula. In other embodiments, the first contact surface has a surface area of about 1.0 to 4.0 mm$^2$. An annular shaped second contact surface surrounding and spaced radially outward and axially from the first contact surface area has a surface area of about 10.0 to 40 mm$^2$. In various embodiments, the skin contact surface of the needle hub has a surface area defined by the first contact surface area and the second contact surface area of about 15.0 mm$^2$ to 50.0 mm$^2$. In one embodiment, the combined surface area of the first contact surface area and the second contact surface area can be about 15.0 to 35.0 mm$^2$. In a further embodiment, the combined surface of the first contact surface area and second contact surface area can be about 15.0 to 20.0 mm$^2$. In a further embodiment, the first contact surface area can have a surface area of about 1 mm$^2$ to 5 mm$^2$, and the second contact surface area can have a surface area of about 10 mm$^2$ to 30 mm$^2$ for provide a combined surface area of about 15 mm$^2$ to about 35 mm$^2$.

The skin contact surface of the needle hub can have a substantially circular shape and a rounded or curved convex profile with the cannula located along the center axis of the circular skin contact surface. The curved or inclined surface of the contact face converges to a center point at the base of the cannula where the cannula extends from the needle hub to define an outer end of the contact face furthest from the base of the contact surface. The cannula in this embodiment has a length of about 4.0 mm to about 6.0 mm to penetrate the skin to a depth and skin layer for delivering the drug, and particularly insulin, to the target depth of the skin for the particular medication. In another embodiment, the cannula has a length of about 3.5 to about 8.0 mm.

In the embodiments shown, the needle hub has a skin contact surface with a substantially convex shape extending from the outer peripheral edge of the hub to the distal axial end of the contact surface of the needle hub at the base of the cannula so that the skin contact surface has a substantially semispherical or conical shape to contact the skin during initial penetration of the cannula and during full insertion for delivery of the drug. The convex surface of the skin contact area of the needle hub can have a width or diameter of about 2.0 to 8.0 mm and an axial height of about 0.5 to about 1.0 mm measured from the outer peripheral edge of the contact surface formed by the outer ring to the outermost center conical portion of the contact surface surrounding the cannula and spaced axially from the peripheral edge. In one embodiment, the axial face forming the convex surface of the needle hub can have a diameter of about 5.0 to 9.0 mm providing a total surface area of about 20.00 mm$^2$ to about 70.0 mm$^2$ and typically about 25.0 to 65.0 mm$^2$. In another embodiment, the axial face has a diameter of about 5.0 to about 7.0 mm.

In one embodiment the convex skin contact surface has a height of about 0.5 mm and a combined or total skin contact surface area of about 15 mm$^2$ to 20 mm$^2$ formed by the first contact surface area and the second contact surface area. The first contact surface and the second contact surface can be spaced apart a distance of about 2 to 3 mm. The height is measured by the axial distance of the outer edge of the needle hub and outer ring to the axial face of the center inner cone shaped member of the needle hub and is generally about 0.5 of 1.0 mm. The total axial surface area of the needle hub is formed by the first contact surface, second contact surface and the area between the first contact surface and the second contact surface can be about 25.0 to 65.0 mm$^2$.

The relationship between the diameter, the height, and total surface area of the contact surface area provides a controlled depth of penetration of the cannula across a range of application forces typically applied to the needle hub when the cannula is inserted into the skin. The needle hub as shown is primarily directed for use with a pen-injector delivery device. In other embodiments, the configuration of the contact surface is suitable for use with reusable or disposable injector devices, autoinjectors, syringes, patch-pumps or other deliver devices that require contact with skin.

In one embodiment of the invention, the skin contact surface of the needle hub has a substantially conical shape with an inner cone shaped member at the center and an outer ring surrounding and spaced radially outward from the inner cone forming an annular recess between. The outer ring in one embodiment forms the outer perimeter edge of the contact face of the needle hub. The recess in one embodiment has a depth that enables the skin to contact the bottom of the recess when the device is pressed against the skin during insertion of the cannula into the skin. In other embodiments, the recess has a depth where the skin does not contact the bottom of the recess. In one embodiment, the depth and radial width of the recess can be configured to form part of the contact surface to control the deformation of the skin surface during penetration of the cannula to control the depth of penetration. The recess can have a depth of about 0.4 to 2.0 mm and generally about 0.4 to 1.0 mm. The recess can be defined by an outer ring at the outer peripheral edge of the needle hub and the inner conical ring member surrounding the cannula at the center of the contact surface. In other embodiments, the recess formed in the skin contact surface can have a volume of about 6 to 35.0 μl.

The inner cone-shaped member forms an inner annular ring having an outer diameter of about 2.0 to about 4.0 mm, typically about 2.0 to 3.0 mm, and an axial contact surface area in the range from about 1.0 to 5.0 mm$^2$. In one embodiment, the outer ring can have an axial surface area of about 10.0 to 35.0 mm$^2$. The inner cone shaped member can form the initial contact surface when the cannula is first inserted into the skin. The inner cone shaped member can have an axial height of 0.3-0.7 mm with respect to the outer edge of the axial face of the outer ring. In another embodiment, the inner cone shaped member can have a axial height of about 0.5 to 1.0 mm with respect to the outer edge of the outer ring. The needle hub can have an initial contact surface area of 1-15 mm$^2$ and a full seating surface area of 5-50 mm$^2$. In one embodiment, the initial contact surface are is formed by the axial face of the inner cone shaped member.

An outer ring forming a second contact surface in one embodiment can have an axial surface area of about 10.0-30.0 mm$^2$ for contacting the skin of the patient. The outer ring can have an axial height from the bottom of the recess of about 0.4 to about 1.25 mm. During the insertion and withdraw of a cannula or needle into the skin of patient causes distortion and deformation of the surface of the skin that influences the penetration of the cannula. Referring to FIGS. 1-7, one embodiment of the invention is needle hub 10 having a body 12 for connecting to a pen needle and a post 14 for supporting a cannula 20 and forming a face for contacting the skin of the patient during insertion and injection. The body 12 has a substantially cylindrical shape with a side wall 16 and a shoulder 18 extending inwardly toward the center axis of the body. In the embodiment shown, the shoulder 18 extends substantially perpendicular to the longitudinal axis of the body.

The post 14 extends axially from the shoulder 18 and is formed with an axial face 24 to support the cannula and define a skin contact surface. Post 18 has an axial height or length to extend from body 12 a distance so that only the face features of the post contact the skin during use. Axial face 24 of post 14 forms the skin contact surface of the needle hub during use. Axial face 24 is formed by a projecting center cone-shaped member 26 that projects axially from post 14 for forming a first portion of the contact surface and the first contact surface. An annular outer ring 28 formed at the perimeter of the post forms the second contact surface area. An annular shaped recess 30 is formed between the center cone shaped member 26 and outer ring 28. The axial face 24 and the skin contact surface are defined by the outer peripheral edge of the outer ring 28 and the inner cone shaped member 26. In the embodiment shown, the annular recess 30 has a bottom surface 34 has a substantially conical shape extending between center cone shaped member 26 and outer ring 28 so that bottom surface 34 extends outwardly from inner member 26 at an incline toward outer ring 28. In the embodiment shown, annular recess 30 has a substantially uniform depth with respect to the inner member 26 and outer ring 28. Bottom surface 34 forms a continuous surface of substantially uniform depth and has a conical curvature that complements the curvature formed by the axial faces of inner member 26 and outer ring 28.

Center cone shaped member 26 extends from the axial face of post 14 to define an axial height greater than an axial height of outer ring 28 relative to the axial dimension of the needle hub as shown in FIG. 1. The height of the center cone-shaped member 26, the height of the outer ring 28 and the differences between the heights contributes to the distortion and deflection of the skin during initial insertion and after the skin relaxes during use to control the depth of penetration of the cannula. The axial spacing between the axial face of cone shaped member 26 and the axial face of outer ring 28 enable center cone shaped member 26 to make the initial contact by the first contact surface with the skin to deform the skin and concentrate the pressure at the center member. The outer ring 28 forming the second contact surface then contacts the skin to limit and control the depth of penetration and deformation of the skin by the difference in height of center cone shaped member 26 by distributing the pressure across the entire width of the axial face.

The center cone shaped member 26 in the embodiment shown has a substantially annular ring-like shape positioned in the axial center of post 14 and extends in an axial direction of post 14. An annular axial surface 38 of the center cone shaped member 26 faces outwardly in the axial direction to form an inner ring and to define the first skin contact portion forming the annular first contact surface of the skin contact surface of the needle hub 10. In the embodiment shown in FIGS. 1-3 and 5, the center cone shaped member 26 has a center recess forming an adhesive well 32 for receiving the cannula and an adhesive for fixing the cannula to the hub 10. The adhesive well 32 has an axial passage for the cannula to extend through the hub for communicating with the pen-injector device. The adhesive well can have a diameter of about 1.5 to 2 mm at the inner edge of the inner cone.

As shown in FIGS. 1-3 and 5, the center cone-shaped member 26 has an annular outer surface 36 that forms a conical shape with an axial face 38. The outer annular surface 36 in the embodiment shown extends substantially in the axial direction and is formed with a slight outward taper. In the embodiment shown, the axial face 38 has a surface extending outwardly with respect to the center longitudinal axis of the needle hub and the center member 26. In the embodiment shown, axial face 38 of center member 26 has a slight curvature forming a conical shape that curves from the inner edge toward the outer peripheral edge of the inner cone shaped member 26 to form a first portion of the conical shaped skin contact surface. As previous discussed, the axial face 38 defines the first contact surface and generally has a surface area of about 1 to about 5 $mm^2$.

The outer ring 28 has a slightly curved axial face 40 with a rounded curved inner edge and a rounded outer edge that converges with the outer annular surface of post 14. The axial face 38 of the center cone shaped member 26 inclines slightly outward toward the peripheral edge of post 14 to form a substantially conical shaped contact surface. The axial face 38 forms the first portion of the contact surface of post 14. The axial face 40 of outer ring 28 forms the second contact surface portion of the contact surface. The radius of curvature of the axial face 38 of the conical shaped member complements the radius of curvature of the axial face 40 of the outer ring 28 and are aligned to form a continuous curve.

The axial face 40 of the outer ring 28 and the axial face 38 of the inner cone shaped member 26 in the embodiment shown are oriented to form a curvature having a radius of curvature of about 6 to about 9 mm. The axial surface 40 of the outer ring can form the second contact surface having a surface area of about 10.0 to about 40.0 $mm^2$. The outer ring 28 and the axial face 40 can have diameter of about 5.0 to 7.0 mm. In one embodiment, axial face 38 can have a substantially flat surface extending perpendicular to the longitudinal axis of the needle hub and perpendicular to the axis of the center cone-shaped member.

In one embodiment, the needle hub has an axial face with a diameter of about 5.0 to about 7.0 mm formed by the inner cone shaped member 26 having the annular axial face 38 with a surface area of about 5.0 to about 10 $mm^2$, the outer annular ring 28 with an annular axial face 40 with a surface area of about 25.0 to 40 $mm^2$, where the combined surface area of the first contact surface formed by the axial face 38 of the cone shaped member 26 and the second contact surface from by the axial face 40 of the outer ring 28 is about 30.0 $mm^2$ to about 50.0 $mm^2$. The inner cone shaped member and the outer ring can be spaced apart a distance of about 1 to 3 mm in one embodiment where the outer dimension of the outer ring and contact surface is about 6-8 mm. In other embodiments, the inner cone shaped member and the outer ring can be spaced apart a distance of about 2 to 3 mm. In another embodiment, the first contact surface can have a surface area of about 5-10 $mm^2$ and the second contact surface can have a surface area of about 10-25 $mm^2$ to provide a combined surface area of about 15-35 $mm^2$. The inner cone shaped member and outer ring can be axially space apart a distance of about 0.3 to 1.0 mm. In another embodiment, the inner ring can be axially spaced about 0.3 mm to 0.7 mm and generally about 0.5 to 1.0 mm.

In a further embodiment, the inner cone shaped member 26 can have a radial width of about 0.8 to 1.2 mm and typically about 1.0 mm as measured from the inner edge to the outer edge of the cone shaped member. The inner cone shaped member can have a surface area in one embodiment of about 3.0 to 4.0 mm. In one embodiment, the inner cone shaped member has a surface area of about 3.5 to 3.7 $mm^2$. The outer ring 28 can have a radial width of about 1.2 to 1.7 mm and generally about 1.5 mm as measured from the outer edge to the inner edge of the outer ring. The outer ring can have a surface area of about 14.0 to 16.0 $mm^2$. In one embodiment, the outer ring can have a surface area of about 15.0 to 15.5 $mm^2$. The needle can also be a 5-bevel needle or cannula.

Figure 5:
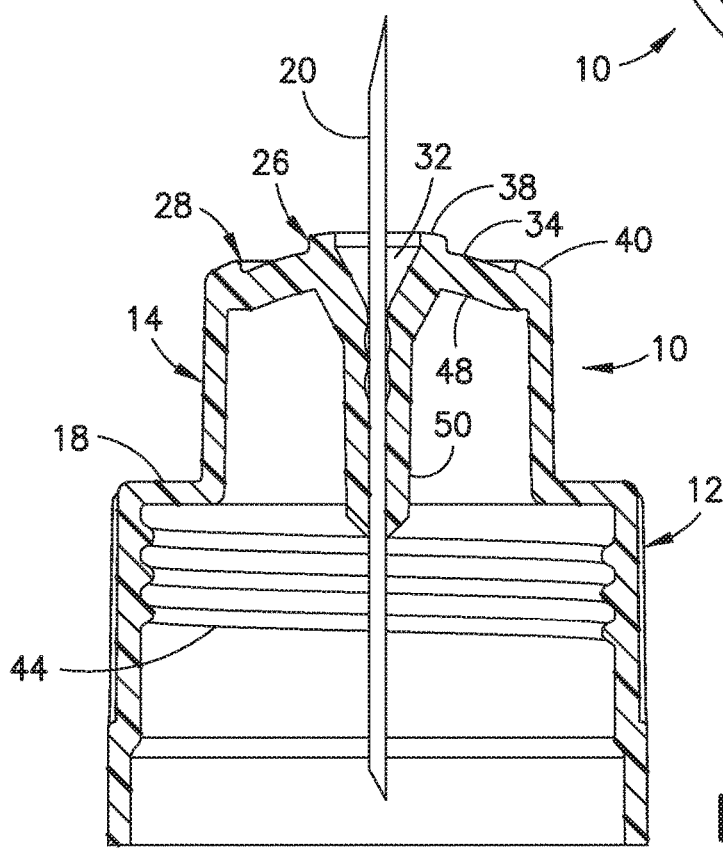
FIG. 5 is a cross section side view of the needle hub.
Figure 6:
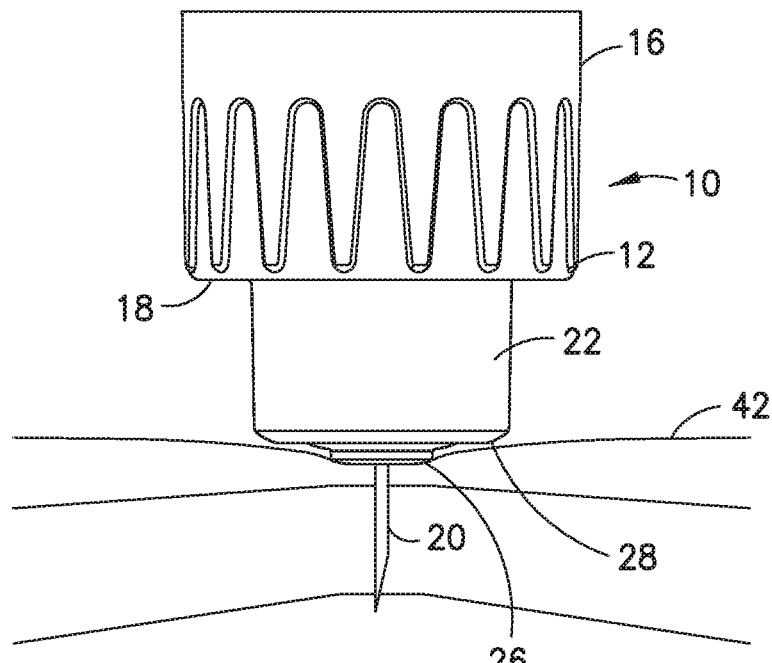
FIG. 6 is a side view of the needle hub showing the initial insertion of the cannula into the skin and the initial penetration depth into the skin.
Figure 7:
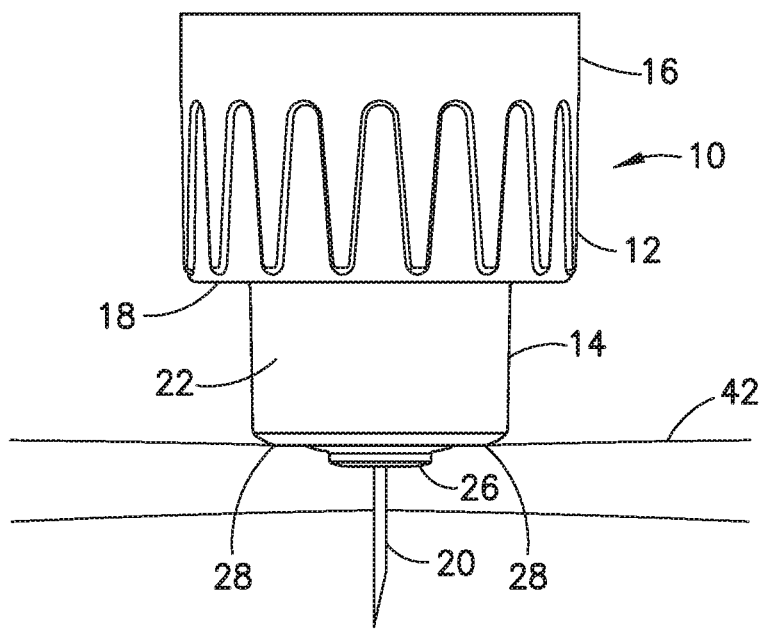
FIG. 7 is a side view of the needle hub showing the cannula inserted into the skin and the skin relaxing to conform to the shape of the end surface of the needle hub and showing the depth of penetration.

As shown in FIGS. 6 and 7, the needle hub 10 contacts the skin 42 of the patient during insertion of a cannula 20 to position the cannula at a desired depth within the skin. As shown in FIG. 5, cannula 20 is inserted into the skin 42 where the axial contact surface of center member 26 makes the initial contact with the skin to depress the skin. Further insertion of cannula 20 results in the axial contact surface of outer ring 28 making contact with the skin 42 to limit deforming of the skin and controlling the depth of penetration of cannula 20 into the skin. Referring to FIG. 6, the inner member 26 of post 14 of needle hub 10 initially contacts the skin 42 producing a distortion of the skin by the downward insertion force. As shown in FIG. 6, the outer ring 28 contacts the skin to increase surface contact with the skin and distribute pressure to limit the depth of penetration. The shape and dimensions of the hub including the height of the center member 26 relative to the outer ring 28 and the combined surface area of the inner member and the outer ring influence the degree of compression and relaxation by the tissue for a given application force. After insertion, the skin 42 relaxes as shown in FIG. 7 so that the cannula tip is at a desired depth for delivering the substance being injected. The depth of penetration may be expressed as follows.

$$f(Depth)=L+l_0*\sigma/E+\psi$$

Where
L=Effective needle length
E=$\sigma/\varepsilon$ Tissue modulus of elasticity
$\sigma=F_n/A$ Compression stress
$\varepsilon=\Delta l/l_0$ Deformation due to applied stress
$F_n$=Normal component force
$A_c$=Cross section interfacing surface area, =f(z)
$l_0$=Uncompressed length
$\Delta l$=Change in length
$\psi$=Tenting factor correction-determined by empirical data
f(z)=Initial Surface Area, Cone Height, Cone Height>z≥0
=Increased surface area, z>Cone Height
*Surface Area (SA) is dependent upon unique face geometry features. Solid models may be utilized to ascertain contacting surface area with respect to needle z-axis translation to enable f(z) function generation.
The one layer tissue model is provided for illustrative purposes of working principle of the invention.

Figure 8:
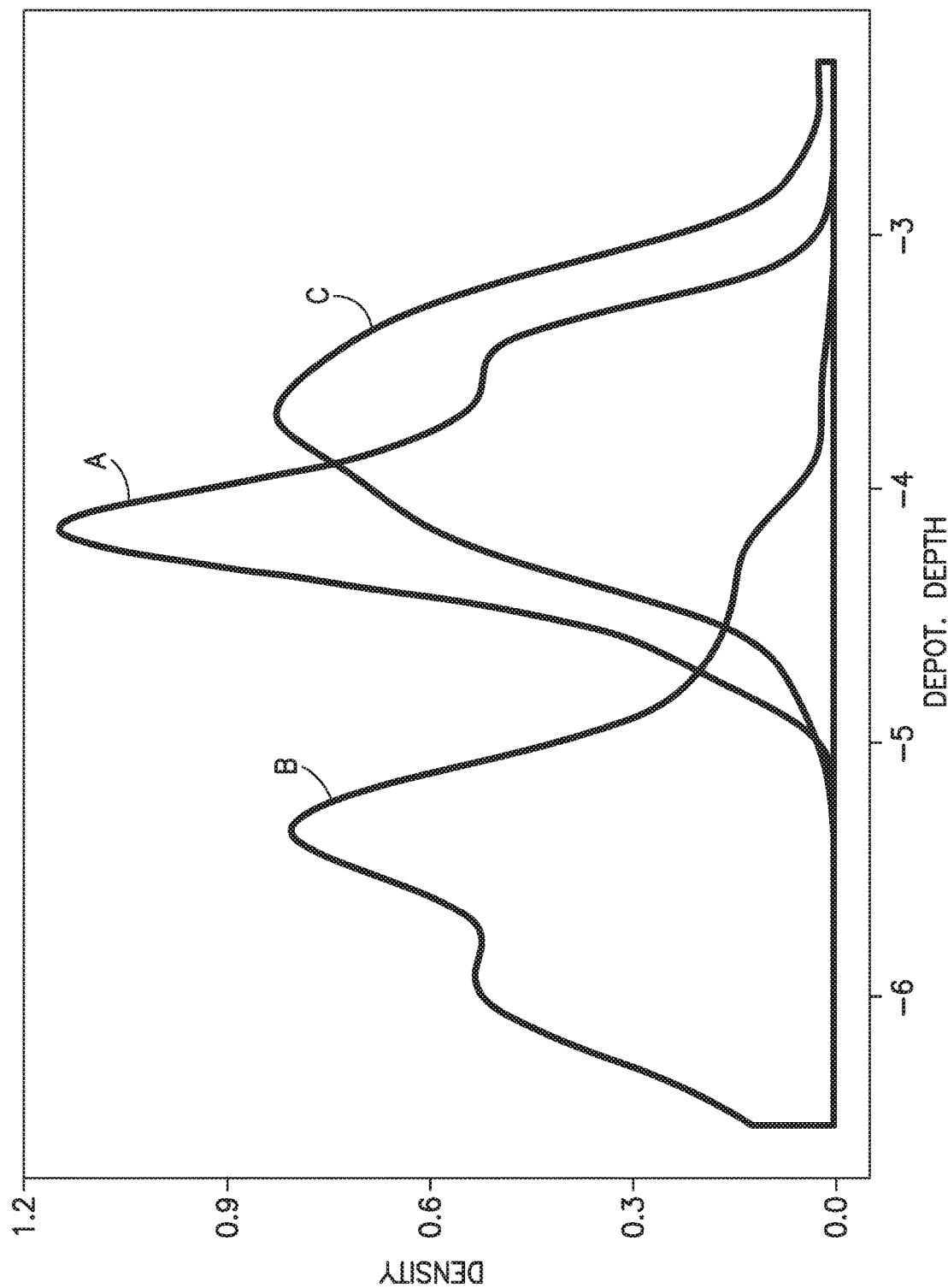
FIG. 8 is chart showing the needle seating depth density distribution.

The needle penetration depth based on the shape and configuration of the skin contact surface is shown in FIG. 8. FIG. 8 is a chart showing the density plot indicating the needle seating within tissue to a specified target depth. In the graph, Device A corresponds to a device as shown in FIG. 1. The measurements were made from the skin surface to the top of 2U depot and represents needle penetration depth in tissue without convolution from inhomogeneous depot dispersion that can occur with larger volume deliveries. Device B and Device C are prior devices. The needle seating depth mean/sd pooled across applied force levels are similar to historical data in which applied force was not measured.

Figure 4:
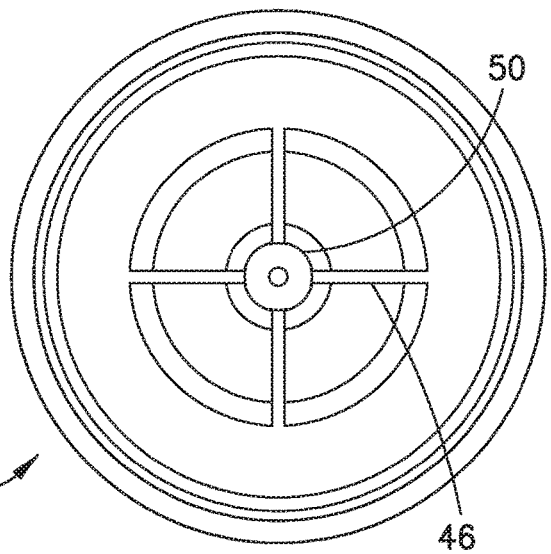
FIG. 4 is a bottom view of the needle hub of FIG. 1.

The needle hub 10 is a configured to be usable with a pen-injector. The body 16 of needle hub 10 as shown in FIGS. 4 and 5 has a wall with threads 44 for connecting to the pen-injector in a typical manner. The cannula 20 extends downward into the center of the needle hub for piercing a septum of a cartridge containing the substance to be delivered. In this embodiment, internal ribs 46 extend form a top wall 48 the entire length of post 14 to provide additional strength and integrity to the needle hub 10. An inner post 50 extends from the top wall 48 a length corresponding to the axial length of post 14 for supporting cannula 20. The ribs 46 extend between the inner surface of post 14 to an outer surface of inner post 50 for supporting post 50 and cannula 20 to resist bending or deflection of cannula 20 and post 50 when connecting to the pen-injector. In the embodiment shown, the ribs 46 have an axial length to stabilize post 50.

A characteristic of a parenteral delivery system is the interface between the device and the delivery site where the tissue biomechanics influences the function of the device. The construction and design of the device accommodates these factors. The complex relationship between the delivery mechanisms, the biointerface and physical and chemical properties of the medicament that determine delivery performance is not well understood. Prior devices generally focus on the features of the needle or cannulas such as length, gauge, penetration three, lubrication and flow characteristics. The pen needle design and face geometries of the needle hub facilitate a consistent needle depth placement within a target tissue space for a specified application. These features provide differentiable configurations to improve comfort during use, reduced risk of intramuscular injections and reduced needle phobia perception. The needle hub face geometry, needle length and gauge, in conjunction with the mechanics of the delivery system and injection technique, determine the success of the device.

The contact surface of the needle hub has a width and height to control the deformation in the skin thereby controlling the depth of penetration of the cannula. The shape and dimension of the contact surface distribute the applied pressure upon full engagement to the skin surface. The contour in combination with the pressure distribution provides improve comfort to the patient. The height and surface area of the hub and the perimeter surface area influence the degree of compression and relaxation of the tissue for a given application force.

In the embodiments described, the center cone shaped member 26 and the outer ring 28 have a substantially cylindrical or annular shape and extend axially from the post 14 where the axial surfaces of center member 26 and outer ring 28 define the skin contact surface of the needle hub 10. The outer ring 28 has diameter to contact the skin during use to control the deformation of the skin in conjunction with the dimensions of the inner cone shaped member 26. In the embodiment shown, the inner cone shaped member 26 has an axial height or length greater than the axial height of outer ring 28 to provide the initial contact with the skin. Contact with the inner cone shaped member 26 is followed by contact with the outer ring 28 upon further insertion of cannula 20 and relaxation of the skin. The dimensions of the inner member and outer ring are selected based on the desired depth of penetration and the length of the cannula. The embodiments described herein are exemplary of the dimension that can be modified as needed to provide a desired depth of penetration of the cannula during use.

The depth of the annular recess 30 can vary depending on the desire depth of penetration by the cannula 20. In the embodiment shown the radial dimension of the annular recess 30 is greater than the combined radial dimension of the inner member and outer ring. Generally the greater the depth of the recess the small contact surface area of the distal face and more deformation of the skin surface enabling deeper penetration by the cannula. The angle of the axial surface of the inner cone and outer ring forming the contact surface can be selected based on the intended result. The annular recess 30 can have a depth with respect to the axial face of the inner member 26 and outer ring 28 so that the skin can contact bottom surface of the annular recess 30 to control skin deformation between inner cone shaped member 26 and outer ring 28. In other embodiments, the depth of annular recess 30 can be sufficiently deep that the skin does not contact the bottom of the annular recess 30 during use.

The needle hub device is suitable for use in a method of reducing shallow injections and for injecting a drug to a patient. The method includes providing a pen body having a medication compartment and a distal end configured for receiving a pen needle. The pen needle includes a hub having base with a recess on a proximal side for receiving and coupling to the pen body. As distal face and an opening extends between the proximal side and the distal face. The above description of the preferred embodiments is not to be deemed as limiting the invention, which is defined by the appended claims. The disclosure is intended to enable the artisan of ordinary skill to practice variants of the invention described without departing from the scope of the invention. Numerical limitations herein, in the specification and in the claims, are understood to be limited by the modifier "about," such that minor departures yielding equivalent results is within the scope of the invention. Features or dependent claim limitations disclosed in connection with one embodiment or independent claim may be combined in another embodiment or with a different independent claim without departing from the scope of the invention.

The invention claimed is:

1. A needle hub configured for coupling to a pen needle delivery device, said needle hub comprising,
   a body with a proximal end and a distal end, said proximal end configured for coupling to the pen needle delivery device, and a post extending from said distal end of said body; and
   a cannula coupled to and extending from said post;
   said post having a first inner surface and an end wall, the end wall having a second inner surface and an outer surface forming a contact surface for contacting a surface of skin of a patient upon insertion of said cannula into the skin of the patient, said contact surface having a first portion surrounding said cannula and forming an inner annular ring forming a first contact surface having a surface area of about 1-5 $mm^2$ and a second portion surrounding and spaced radially outward from said first portion forming an outer annular ring forming second contact surface, and an annular recess extending between said inner annular ring and said outer annular ring, where said first contact surface and second contact surface have a combined surface area of about 15-50 mm² and provide consistent delivery over a range of insertion forces;
said end wall having an inner post extending from the second inner surface toward said proximal end of said body, wherein a plurality of ribs extend between the inner post and the first inner surface for stabilizing the inner post.

2. The needle hub of claim 1, wherein said inner annular ring and said outer annular ring are spaced apart about 2-3 mm to form said annular recess between said first contact surface and said second contact surface, and said inner annular ring has a radial width of 0.8 to 1.2 mm and a surface area of 3.5 to 3.7 mm².

3. The needle hub of claim 2, wherein said first contact surface is positioned to contact the skin of the patient upon insertion of said cannula deforming the surface of the skin and where second contact surface contacts the skin upon deflection of the skin contacting said first contact surface.

4. The needle hub of claim 3, wherein said contact surface of said needle hub has a substantially conical configuration with an axial height complementing said combined surface area to enable said cannula to penetrate the skin at a predetermined depth.

5. The needle hub of claim 4, wherein said cannula has a length and gauge complementing the axial height of said contact surface and combined surface area to enable said cannula to penetrate the skin to a predetermined depth.

6. The needle hub according to claim 1, wherein the first contact surface has a curved surface adjacent the cannula having a diameter of 2 mm to 3 mm, and the second contact surface has an outer diameter of about 5.0 to 7.0 mm.

7. The needle hub according to claim 1, wherein said contact surface of said post has a substantially convex surface extending between a peripheral outer edge of said post and said cannula.

8. The needle hub according to claim 1, wherein said first contact surface surrounding said cannula has a radius of curvature complementing the radius of curvature of said second contact surface.

9. The needle hub according to claim 1, wherein said cannula has a length of about 3.5 to about 8.0 mm.

10. The needle hub according to claim 1, wherein said inner annular ring extending from a distal surface and has an axial distal face with a radial width to define said first contact surface to contact the surface of the skin during insertion of the cannula into the skin of the patient, and said outer annular ring has a surface area of 10-25 mm² and said combined surface area is 15 to 35 mm² and said inner annular ring and outer annular ring are axially spaced 0.3 to 0.7 mm.

11. The needle hub according to claim 1, wherein said inner annular ring and outer annular ring are aligned in a continuous curve.

12. The needle hub according to claim 11, wherein said annular recess has a continuous convex surface aligned with an axial face of said inner annular ring and axial face of said outer annular ring.

13. The needle hub according to claim 12, wherein said annular recess has a depth of about 0.4 to 1.0 mm.

14. The needle hub according to claim 11, where said inner annular ring and said outer annular ring are spaced apart about 2-3 mm and where said contact surface has a diameter of about 5-8 mm.

15. The needle hub according to claim 1, wherein said inner annular ring and said outer annular ring have a combined surface are of about 15-35 mm².

16. A method for injecting a medication to a subject, comprising
a pen body having a medication compartment and a distal end configured for receiving a pen needle, the pen needle comprising
a needle hub having a body for coupling to the pen body, a distal surface and an opening extending between a proximal end and said distal end with an axially extending post, a cannula coupled to said post, where said post has a first inner surface and an end wall, the end wall having a second inner surface and an outer surface forming a contact surface for contacting a surface of skin of the subject, said contact surface having an inner annular ring surrounding the cannula and forming annular first contact surface having a surface area of about 1-5 mm² and an outer annular ring surrounding and spaced radially outward from said inner annular ring forming an annular second contact surface with a surface area of 10-25 mm², and an annular recess between said inner annular ring and outer annular ring, where the first contact surface and second contact surface have a combined surface area of about 15-35 mm², wherein the end wall has an inner post extending from the second inner surface toward the proximal end of the body, and a plurality of ribs extend between the inner post and the first inner surface for stabilizing the inner post; and
inserting said cannula into the skin of the subject where the first and second contact surfaces contact the subject's skin to limit depressing and deforming of the skin to control a depth of penetration of the cannula.

17. The method according to claim 16, wherein said annular recess has a continuous convex bottom surface concentric with said inner annular ring and outer annular ring.

18. The method according to claim 16, wherein said inner annular ring has a substantially planar surface surrounding said cannula and extending in a plane substantially perpendicular to an axis of said cannula, and where said outer annular ring forms a continuous convex surface extending between a peripheral edge of said post and a peripheral outer edge of said planar surface.

19. The method according to claim 16, wherein said inner annular ring has a radial width of 0.8-1.2 mm and a surface area of 3.5-3.7 mm².

20. The method according to claim 19, wherein said outer annular ring has a radial width of 1.2-1.7 mm and a surface area of 14-16 mm².

21. The needle hub of claim 1, wherein the plurality of ribs extend from the second inner surface of the end wall of the post an entire length of the post.

* * * * *